| United States Patent [19] | [11] | 4,141,973 |
|---|---|---|
| Balazs | [45] | Feb. 27, 1979 |

[54] ULTRAPURE HYALURONIC ACID AND THE USE THEREOF

[75] Inventor: Endre A. Balazs, Riverdale, N.Y.

[73] Assignee: Biotrics, Inc., Riverdale, N.Y.

[21] Appl. No.: 844,833

[22] Filed: Oct. 25, 1977

Related U.S. Application Data

[63] Continuation of Ser. No. 623,333, Oct. 17, 1975, abandoned.

[51] Int. Cl.$^2$ .................. A61K 31/70; C07G 3/00
[52] U.S. Cl. ..................................... 424/180; 536/4
[58] Field of Search ............... 424/180; 260/209 R, 260/705

[56] References Cited

PUBLICATIONS

Chem. Abst. 55, 4892(c) (1960).
Chem. Abst. 52, 16442(a) (1958).
Chem. Abst. 70, 326(f) (1969).
Chem. Abst. 67, 25397(f) (1967).
Chem. Abst. 54, 13237(a) (1960).
Chem. Abst. 48, 10826(h) (1954).
Chem. Abst., 8th Collective Index, pp. 15074(s)–15076(s), (1972).
Arch. Ophth. 88(11) pp. 544–548 (1972), Constable et al.
Invest. Ophth. 11(3) pp. 164–168 (1972), Swann et al.
Balaz et al., Mod. Probl. Ophthal. 10, pp. 3–21 (1972).
Regnault et al., Mod. Probl. Ophthal. 12, pp. 378–383 (1974).
Balaz et al. (New & Controversial Aspects of Retinol Detachment) pp. 371–376 (1968).
Castren, ACTA Opthth. 42.
Morean et al., Ann. Oculist., pp. 493–501, (1968).
Girod et al., Ann. Oculist., pp. 25–40, (1970).

Primary Examiner—Albert T. Meyers
Assistant Examiner—D. W. Robinson
Attorney, Agent, or Firm—Hubbell, Cohen, Stiefel & Gross

[57] ABSTRACT

An ultra-pure, high molecular weight hyaluronic acid fraction which is characterized by the absence of significant cellular infiltration of the vitreous and anterior chamber, absence of significant flare in the aqueous humor, absence of significant haze or flare in the vitreous and absence of pathological changes to the cornea, lens, iris, retina, and choroid of the owl monkey eye when one milliliter of a 1% solution of the sodium salt thereof dissolved in physiological buffer is implanted in the vitreous replacing about one-half the existing liquid vitreous. This material is obtained from animal tissue containing hyaluronic acid by a process which comprises removing the blood from animal tissue containing hyaluronic acid, extracting hyaluronic acid therefrom, deproteinizing the hyaluronic acid extract, and removing any unidentified inflammation causing agents persent therein by treating the deproteinized hyaluronic acid extract at a pH of 6.0 – 7.0 with a volume of chloroform at least about equal to that of the deproteinized extract, to form a two-phase mixture which is then stirred, sufficiently to ensure intimate contact between said two phases, at about 15° – 40° C., followed by separating out and discarding the chloroform phase.

11 Claims, No Drawings

ULTRAPURE HYALURONIC ACID AND THE USE THEREOF

CROSS REFERENCE TO RELATED APPLICATIONS

This is a continuation, of application Ser. No. 623,333, filed Oct. 17, 1975 now abandoned.

BACKGROUND OF THE INVENTION

1. Field of the Invention

The invention relates to an ultrapure, high molecular weight hyaluronic acid, generally, but not necessarily in the form of the sodium salt (hereinafter referred to as "HUA"), obtained from animal connective tissue such as rooster combs, human umbilical cords, or from bacteria culture which is suitable for use as a biologically active therapeutic injection, implant or infusion because of its non-inflammatory properties when so used. As used herein, in connection with the HUA of this invention, non-inflammatory signifies the absence of significant cellular infiltration of the vitreous and anterior chamber, absence of significant flare in the aqueous humor, absence of significant pathological changes to the cornea, lens, iris, retina and choroid of the owl monkey eye when an HUA preparation is tested in accordance with the modified owl monkey test described below.

The invention also relates to processes for obtaining such product and the use thereof.

2. The Prior Art

HUA is a naturally occurring high viscosity glycosaminoglycan having alternating $\beta$ 1-3 glucuronidic and $\beta$ 1-4 glucosaminidic bonds. The molecular weight of this material is generally within the range of 50,000 to 8,000,000 (although there are reports of HUA having molecular weights as high as 13,000,000) depending on the source, method of isolation and method of determination. It is found in animal tissue, e.g., in umbilical cord, vitreous humor, synovial fluid, rooster combs, pathologic joints, group A and C hemolytic streptococci and in skin.

The isolation and characterization of HUA is described in Meyer et al, J. Biol. Chem. 107, 629 (1934); J. Biol. Chem. 114, 689 (1936); Balazs, Fed. Proc. 17, 1086 (1958); Laurent et al; Biochim. Biophys. Acta 42, 476 (1960). The structure of HUA was elucidated by Weissman et al, J. Am. Chem. Soc. 76, 1753 (1954) and Meyer, Fed. Proc. 17, 1075 (1958).

It has long been an object of medical researchers to obtain an HUA preparation from animal tissues which could be used as a substitute or partial substitute for the naturally occurring HUA in vitreous humor and/or synovial fluid. Moreover, a suitable HUA preparation has long been sought for other medical applications wherein there is a depletion of the naturally occurring fluids containing HUA and consequently, the need for a replacement for such fluids.

There is, therefore, a large body of literature describing so-called purified HUA and various techniques for purifying naturally occurring HUA. There are many high molecular weight purified HUA preparations which are described in the literature; however, none of these preparations is suitable for the above-described uses because there is some unidentified impurity present in all of them which causes severe inflammation when the preparation is injected into a mammalian body and particularly, the eyes, for the purpose of providing a substitute for a natural material such as vitreous humor. The preparation according to the invention does not contain this impurity because when it is used as a substitute for the naturally occurring material, no such inflammation is observed. To date, I have been unable to identify this impurity, although I am able to effectively demonstrate its presence in previously known preparations and its absence from the present preparation as will appear below.

There will now follow a description of the most relevant prior art of which I am aware.

In two publications by Balazs and Sweeney, there is described certain work done by them on the therapeutic use of so-called "reconstituted vitreous" which is a mixture of human collagen and human HUA. This reconstituted vitreous contains only a relatively low concentration of HUA, i.e., 0.1–0.3%, and thus, it was not of critical importance that the HUA be extremely pure. This work is described in (1) New and Controversial Aspects of Retinal Detachment, Chapter 36: "The Injection of Hyaluronic Acid and Reconstituted Vitreous into the Vitreous Cavity,38 pages 371–376. Hocher Medical Division, Harper & Row, 1968; and (2) The Replacement of the Vitreous Body in the Monkey by Reconstituted Vitreous and by Hyaluronic Acid, Mod. Probl. Ophthal., Vol. 4, pp. 230–232, 1966. These papers describe the use of an HUA preparation which was thought at the time to be acceptable because "Postoperative reaction in the anterior chamber (of the monkey eye) showed a slight flare and a little fibrinous precipitation which disappeared in the majority of cases after several days" Mod. Probl. Ophthal., page 230. It is to be noted of course, that fibrous precipitate in the anterior chamber is the result of excessive inflammatory reaction and consists of precipitated fibrin and agglomerated inflammatory cells. It has since been learned that the HUA preparation described in these references contained far too much of the unidentified inflammatory fraction of HUA. The preparatory method decribed in these publications will not lead to the obtention of an HUA free of inflammatory fractions.

A series of publications by Constable and Swann:

(1) Biological Vitreous Substitutes — Inflammatory Response in Normal and Altered Animal Eyes, Arch. Ophthal., 88, Nov. 1972, 544–548;

(2) Vitreous Structure II Role of Hyaluronate, Invest. Ophthal., 11, No. 3, pp. 164–168, 1972; and (3) Vitreous Substitution, Retina Congress, Eds. Pruit and Regen, Appleton, Century and Croft, 1974, pps. 709–713, describes the preparation and use (as a vitreous substitute) of a purified HUA. This preparation, which is somewhat similar to mine is, nevertheless not characterized as a vitreous substitute because it too is characterized by the presence of some unidentified inflammation causing impurity. Thus, on page 545 of the Arch. Ophthal. article, the authors state that "Hyaluronic acid in normal eyes caused a maximal 2+ or 3+ inflammatory response at two days (FIG. 1) which subsided clinically over seven to ten days. At two days the mean vitreous cell count was 1,194/cu mm and the protein concentration five times normal. Both cell counts and protein concentration rapidly fell to normal over three weeks." Moreover, on page 711 and 712 of Vitreous Substitution they state that "In normal owl monkey eyes [HUA] causes a mild acute inflammatory response" and that therefore, "It is apparent that with [HUA] all the fluid vitreous must be replaced and inflammation must be supressed with systemic anti-inflammatory agents." Indeed, in FDA Interim Report — Project No. 8746 (Nov. 1973), it is stated, on page 4 that "An inflammatory reaction in vitreous cavity was universally observed following the implantation of Hyvisc* [their HUA preparation]."

* Produced by Med-Chem Products, Inc., Boston, Mass.

All of the HUA preparations described in the prior art of which I am aware are characterized by the presence of an as yet unidentified inflammation inducing material. The presence of this material can be readily demonstrated by the modified owl monkey eye test described below.

SUMMARY OF THE INVENTION

The present invention has among its objects, the provision of a new, ultrapure HUA which is non-inflammatory, as well as processes for obtaining such product, and uses thereof.

I have now been able to obtain such a product from connective tissues, physiological solutions of which demonstrate therapeutic value in the treatment of pathologies of connective tissue fluids — primarily via replacement of or acting in concert with the existing hyaluronic acid macromolecules in these pathological fluids.

In order to have therapeutic activity, the concentration of HUA in a therapeutically active solution should be at least the same magnitude as that which is found in normal tissue fluids, namely 0.2–0.3%. It is preferable that the concentration of HUA in the therapeutic solution be higher than in normal tissue fluids, i.e., about 1%.

The exact nature of the therapeutic action of HUA in the treatment of connective tissue diseases is not fully understood. However, in vitro biological activity of HUA (inhibition of cell migration and multiplication of certain cells) has been demonstrated. It is believed that this biological activity is partly responsible for the therapeutic activity of these solutions.

The biological activity of HUA solutions depends generally on a combination of the molecular weight and conformation of the HUA molecules and the concentration of these molecules in solution. There is an inverse relationship between HUA molecular weight and concentration, such that higher concentrations of smaller HUA molecules are required to achieve a given level of biological activity. The preferred combination according to the invention is a HUA molecular weight of at least about 750,000, preferably at least about 1,200,000 and a concentration of at least about 0.5%. However, this simple concentration — molecular weight relationship is not sufficient to completely explain the biological activity of HUA solutions. The conformation of the HUA in solution, as measured by molar optical rotary dispersion, modifies this relationship. HUA molecules that demonstrate pronounced conformational ordering with increasing concentration also show enhanced biological activity.

As a consequence of the above considerations, therapeutically valuable HUA solutions would have to be relatively concentrated, containing high molecular weight HUA with pronounced conformational ordering of the macromolecules in the solution.

However, it has been found that, in general, concentrated solutions of heretofore known purified HUA are not tolerated by the connective tissue spaces of the body and evoke an immediate (within 48 hours) inflammatory response. Inflammatory reaction will occur, of course, if the purified HUA contains microorganisms, proteins and/or pyrogens. However, even sterile, pyrogen free known HUAs of the highest purity (less than 0.05% protein content) cause inflammation. This inflammatory activity is not related to the chemical purity of the HUA as measured by standard analytical chemical methods.

By using dilute solutions of HUA the inflammatory activity is reduced to a low enough level so that the body's inflammatory response is not significant. However, such dilute solutions of HUA do not exhibit significant biological activity or therapeutic value.

Thus, the principal object of the invention is an isolated fraction of HUA (1) of high molecular weight, (2) specific conformational quality which is (3) essentially free of proteins, peptides and nucleic acid impurities (4) is sterile and pyrogen free and (5) whose concentrated solutions do not cause an inflammatory reaction, when implanted in animal or human connective tissues spaces. A further object of the invention is a process by which this non-inflammatory HUA fraction is extracted from various connective tissues. A further object of the invention is the use of concentrated physiological solutions of this non-inflammatory fraction of HUA for treatment of diseases and injuries to connective tissues.

The product according to the invention is a sterile, pyrogen-free, non-antigenic, high molecular weight hyaluronic acid fraction being characterized by the absence of significant cellular infiltration of the vitreous and anterior chamber, absence of significant flare in the aqueous humor, absence of significant haze or flare in the vitreous and absence of pathological changes to the cornea, lens, iris, retina, and choroid of the owl monkey eye when one milliliter of a 1% solution of the sodium salt thereof dissolved in physiological buffer is implanted in the vitreous replacing about one-half the existing liquid vitreous.

In more detail the product according to the invention is a HUA fraction having (a) an average molecular weight greater than about 750,000, preferably greater than about 1,200,000 — that is, a limiting viscosity number greater than about 1400 cm$^3$/g., and preferably greater than about 2000 cm$^3$/g., (b) a protein content of less than 0.5% by weight, (c) ultraviolet light absorbance of a 1% solution of sodium hyaluronate of less than 3.0 at 257 nanometers wavelength and less than 2.0 at 280 nanometers wavelength, (d) a kinematic viscosity of a 1% solution of sodium hyaluronate in physiological buffer greater than about 1000 centistokes, preferably greater than 10,000 centistokes, (e) a molar optical rotation of a 0.1–0.2% sodium hyaluronate solution in physiological buffer of less than $-11 \times 10^3$ degree — cm$^2$/mole (of disaccharide) measured at 220 nanometers, (f) no significant cellular infiltration of the vitreous and anterior chamber, no flare in the aqueous humor, no haze or flare in the vitreous and no pathological changes to the cornea, lens, iris, retina, and choroid of the owl monkey eye when one milliliter of a 1% solution of sodium hyaluronate dissolved in physiological buffer is implanted in the vitreous replacing approximately one-half the existing liquid vitreous, said HUA being
(g) sterile and pyrogen free and
(h) non-antigenic.

Properties (a), (d), and (e) are related to the biological activity and thus, it is theorized, the therapeutic activity of the HUA fraction according to the invention. Properties (b), (c), (f), (g) and (h) measure the purity and non-inflammatory activity of the fraction which control its suitability for therapeutic implantation.

Each of the above properties labelled (a)-(h) will now be discussed.

(a) Molecular Weight

HUA extracted from tissue is polydisperse with respect to molecular weight. The fraction which is the object of this invention is also polydisperse, containing HUA molecules covering a range of molecular weights. The measured molecular weight is thus an average value for the molecules in the collected fraction. The average value of at least about 750,000 is the weight average molecular weight.

The average molecular weight can be measured either directly or indirectly. An indirect method, the limiting viscosity method, which essentially measures the increase in viscosity of a solution is utilized because of its ease. See, e.g., Physical Chemistry of Macromolecules by Charles Tanford, John Wiley & Sons, Inc., New York (1961), pps. 407-412. The weight average molecular weight is calculated from the limiting viscosity number by the published equation of Laurent et al, Fractionation of Hyaluronic Acid, Biochimica et Biophysica Acta, 42, (1960), pps. 476-485.

(b) Protein Content

During the extraction of HUA from the tissue source, proteins are simultaneously extracted. Since proteins are antigenic, it is essential, for therapeutic applications, to isolate a HUA fraction which is essentially protein free.

A well known, highly sensitive colorimetric method is used to detect proteins in the isolated HUA fraction; Lowry et al J. Biol. Chem., 193, 265-275 (1951).

At one time, published reports suggested protein free HUA could not be obtained without a significant decrease in the molecular weight of the HUA. However, a few studies have shown that substantially protein free high molecular weight HUA does indeed exist; Laurent, Structure of Hyaluronic Acid pp. 703-732 in Chemistry and Molecular Biology of the Intercellular Matrix, edited by Balazs; Acadamic Press, 1970; Balazs et al, Viscosity of Hyaluronic Acid Solutions Containing Proteins, Acta Societatis Medicorum Upsaliensis, 64 3-4 pp. 137-146 (1959).

(c) Ultraviolet Absorbence

Ultraviolet spectroscopy is used to show the absence of nucleotides (DNA and RNA) in the HUA fraction. The solution used for measurement is arbitrarily taken as a 1% HUA (w/v) in 0.15 molar NaCl. The absorbence at a wavelength of 257 nanometers measures the level of nucleotides in the solution.

Also, the absorbence of the solution at a wavelength of 280 nanometers can be used to measure the level of protein in the solution.

(d) Kinematic Viscosity

The concentration of HUA in tissue fluids is normally greater than 0.1%. At these concentrations the HUA molecules are crowded together and interact with each other. The viscosity of the solution is dependent on this intermolecular interaction. To characterize the intermolecular interaction of the HUA fraction of the invention, the kinematic viscosity at 25° C. of a solution of 1% HUA in physiological buffer is utilized. Under these conditions, the viscosity of the HUA fraction has a minimum viscosity of 1000 centistokes, and preferably of 10,000 centistokes, that is 10,000 times the viscosity of the solvent.

(e) Optical Rotary Dispersion

The optical rotary dispersion measurement of HUA and its salt indicate an ordered structure of the molecule. The value of molar optical rotation in most polymers is independent of the concentration of the solution on which the measurements are carried out. In case of sodium hyaluronate it has been shown (Chakrabarti et al, J. Mol. Biol. (1973) 78, 135-141) that in preparations with high molecular weight the molar rotation changes, becoming more negative with increasing concentration.

(f) Absence of Inflammatory Activity

It is well known that impurities present in sterile purified HUA will cause an immediate cellular reaction if implanted in connective tissue. These inflammatory impurities were generally thought to be of three types: proteins and peptides; nucleoproteins and nucleic acids; and pyrogens. However, it has been discovered that, in general, even HUA which, by presently available analytical techniques appears to be free of these impurities will cause cellular reaction when implanted in therapeutically useful concentrations. Using the process according to the invention, a fraction of HUA that is free of inflammatory activity has been isolated.

Although a sensitive test which is described below has been developed to discriminate between the non-inflammatory HUA fraction of the invention and other, purified HUA fractions, the chemical nature of the inflammatory agent in purified HUA has not as yet been identified. The following information has been obtained regarding this inflammatory agent.

This agent is not an inflammatory impurity of the protein, peptide, or nucleotide families as measured by standard analytical methods. Isolated HUA fractions of equivalent high purity may or may not cause cellular reaction independent of their purity.

Gas chromatographic analysis shows that the inflammatory activity is not due to residual solvents or chemicals originating from the purification process of the HUA. Thus, the activity is not the result of an inflammatory agent added during processing.

Dialysis, which removes smaller molecules of less than 10,000 molecular weight, does not remove the inflammatory agent. This is further evidence that the inflammatory activity is not the result of a lower molecular weight impurity either extracted from tissue during purification or added during the purification process.

The inflammatory activity is not related to the size of the HUA molecule as measured by limiting viscosity number, nor is it related to the interaction between HUA molecules as measured by the kinematic viscosity of the solution.

Infrared spectroscopy of non-inflammatory and inflammatory HUA samples shows no difference in the spectra of the two HUA fractions and further shows no difference from the published spectra of HUA. Consequently, the inflammatory agent is an HUA moiety or another component attached to the HUA at an undetectable concentration.

Without intending to be bound thereby, I have theorized that there may be two forms of HUA in connective tissue: one inflammatory and one non-inflammatory. In normal tissue, which is the source of purified HUA, the inflammatory fraction exists in low concentration where its activity is not significant. However, during isolation and purification procedures, typically 50 percent of the HUA is lost. Consequently, the proportion of inflammatory active HUA can increase in the purified samples, unless removal of the inflammatory agent is effected by the purification process.

Although the inflammatory HUA agent or fraction cannot be identified by analytical chemical methods, I have developed a highly discriminatory test which demonstrates the non-inflammatory HUA fraction of the invention.

This test involves the replacement of approximately one-half the liquid vitreous of the owl monkey with a 1% solution of hyaluronic acid and measuring the invasion of white blood cells into the vitreous and anterior chamber, the flare in the aqueous humor, the haze and flare in the vitreous, and pathological changes to the cornea, lens, iris, retina, and choroid 48 hours after injection. The HUA fraction of the invention will not cause any cellular invasion over and above that amount caused by the trauma of the operation itself — namely, 2–70 white blood cells per $mm^3$ of aqueous humor or vitreous - nor will there occur any flare in the aqueous humor, haze or flare in the vitreous, or pathological damage to the cornea, lens, iris, retina and chorid. However, in the normal manufacturing practice, different batches of HUA prepared according to the invention can be expected to exhibit varying degrees of successful separation of the inflammatory active HUA from the non-inflammatory fraction of the invention. Consequently, an upper limit of about 200 white cells per $mm^3$ aqueous humor or vitreous, slight flare in the anterior chamber, and slight haze and flare in the vitreous have been arbitrarily selected, above which it is concluded that too high a proportion of inflammatory active agent exists in the product of the invention for therapeutic application.

It is important to note that the preparation of a non-inflammatory HUA fraction which can pass the monkey test is unique and nowhere suggested in the prior art. Swann (Arch. Ophthal., 88, 1972 pp. 544–8) reports a high molecular weight HUA (1,200,000) of very high purity, i.e., less than 0.05 percent protein. However, he found cell counts of nearly 1,200 per $mm^3$ vitreous in the monkey test, even using a solution of 0.62% HUA.

The owl monkey eye test used to establish the non-inflammatory nature of the HUA of the invention will now be described in detail.

Vitreous Test in the Douroucoulis Monkey Eye

The Douroucoulis monkey (owl monkey, aotus trivirgatus) is used for this test*. The adult (700–1000 g. body weight) monkey is anesthetized intramuscularly with 2.5 mg. pentobarbital per 100 g. body weight. After 30 minutes, if sedation is not adequate, additional supplements are given in increments of 0.25 mg. pentobarbital per 100 g. body weight.

* This monkey has a liquid vitreous which facilitates the exchange of the vitreous with minimal trauma.

The monkey eye is dilated at the time of the initial pentobarbital injection with three drops of 1% ophthalmic cyclopentolate HCl. After the eye is fully dilated (approximately 20 minutes), it is first examined with a slit lamp. The cornea, anterior chamber, lens and iris are observed first. The anterior chamber must be free of cells and flare and no opacities should be present in the lens. Any abnormalities in the cornea or iris should be noted. The vitreous should be examined for flare, cells and precipitates. With the indirect ophthalmoscope, the vitreous and the retina are examined. Careful note must be made of the condition of the optic disk and its periphery. Any scars or areas of pigmentation must be noted. The clarity of the vitreous is recorded. If the vitreous or retina show any abnormalities with this examination, the monkey is not used.

The orbital area of the monkey is then shaved with curved scissors. Special attention is given to preparing the lateral orbital area. The cut hair is removed with a wet sponge, and the monkey is taken to the surgical operating table where the following procedures are carried out under sterile conditions. The surgeon prepares his hands with a surgical scrub, then in sterile gloves prepares the skin of the monkey at the periorbital area, by swabbing with a cotton-tipped swab soaked in 1% iodine. The eye (including the cul de sacs) is then lavaged with sterile saline and is dried with sterile cotton swabs. The area is draped with a sterile plastic drape, and a hole is cut so that only the surgical area is exposed.

The skin is cut by performing a temporal canthotomy. The skin incision is extended for a distance of 5–8 mm. The lateral orbital bone is exposed and the skin and subcutaneous tissue are dissected free from the bone. A triangular piece of bone (exposing a 5 × 5 mm. area) is then cut away with heavy scissors. The conjunctiva of the globe is then excised and freed from the sclera in the direction of the limbus. The integrity of the conjunctivallimbal junction is not impaired. This makes the risk of post-operative infection much less. After a small area of the sclera is exposed by extending the conjunctival incision laterally, the sclera is cauterized at a point 5 mm. from the limbus using a blunt-tipped glass rod heated in an alcohol flame. In this area two parallel continuous sutures are placed with a loop between them. Care is taken not to perforate the globe. The first part of the square knot is tied and tightened so that it rests on the loop left between the two sutures. A syringe of the HUA is placed under sterile conditions on a sterile towel. A 25 G needle connected to a flexible tube (butterfly pediatric infusion set, catalog No. 4573, Abbott Lab., Chicago Illinois) is inserted through the pars plana ciliaris (5 mm. behind the limbus) into the center of the vitreous.

Then 0.9–1.1 ml. of the vitreous (approximately one-half the total volume) is withdrawn by using a 2.5 ml. sterile syringe. The withdrawn vitreous is replaced by an equal volume of HUA. During this operation the 25 G needle must be held without moving it in an angle directed toward the peripheral part of the vitreous cavity (in order not to pull the Cloquet's canal) but not touching the retina. The withdrawal and injection should be done slowly. The scleral wound is closed by pulling the preplaced suture tightly and completing the square knot.

The area of the wound is lavaged with sterile saline and the wound site is dried with sterile cotton-tipped swabs. The conjunctival wound is then closed with a single 7-0silk suture. When closing the skin incision, care is taken to approximate the temporal canthal area first, and then the remainder of the skin is sutured with three interrupted sutures of 7-0 silk. The wound is sprayed with Rezifilm ® surgical spray (Squibb). The eye is then examined by indirect ophthalmoscopy and slit lamp to check possible hemorrhage in the vitreous. If such hemorrhage is found, the eye cannot be used for evaluation of the HUA.

After examination, two drops of 1% ophthalmic atropine are placed in the eye and ophthalmic erythromycin ointment is placed beneath the lids.

Observation of the monkey takes place 48 hours after surgery. The monkey is anesthetized with an intramuscular injection of ketamine HCl (12 mg./kg.). Adequate sedation for examination should be achieved within 5 minutes.

Using the indirect ophthalmoscope, the cornea is examined for haze and the iris for signs of inflammation (discoloration and redness). The lens is then examined for injury from the previous surgical procedure.

The anterior chamber is examined with slit lamp for flare and this is recorded as 0, 1, 2, 3 (none, slight, moderate, severe).

The fundus (retina and choroid) and the vitreous are then examined with the indirect ophthalmoscope. The clarity of the vitreous in terms of haze and the presence of hemorrhage is evaluated. The haze in the vitreous is evaluated as 0) none; 1) slight haze, but clear fundus; 2) haze, fundus just visible; 3) haze, red fundus reflection, fundus not visible; and 4) haze, grey fundus reflection, fundus not visible. With slit lamp the vitreous is then evaluated for flare on a scale of 0, 1, 2, 3 (none, slight, moderate, severe). The cells in the vitreous are estimated with the slit lamp on a scale of 0, 1, 2, 3 (none, few, numerous, many). The retina and choroid are examined for bleeding and scars caused by the operation.

The ocular cul de sacs are then lavaged with sterile saline. Under sterile condition 0.2 cc. aqueous is removed by passing a 27 G ½ inch needle, with a tuberculin type plastic syringe attached, anterior to the limbus into the aterior chamber. Care is taken not to come into contact with the iris, lens, or endothelium of the cornea. A small volume of vitreous (0.1-0.4 ml.) can be withdrawn by the same method as described for the HUA injection procedure. The removed vitreous is replaced with physiological buffer solution or HUA. The cell content of the small vitreous sample is counted after dilution, with equal volume of physiological NaCl that contains a small amount of hyaluronidase in order to decrease the viscosity of the solution. The aqueous humor removed from the anterior chamber is placed in a blood counting chamber without dilution and a count of white cells performed. The appropriate conversion factors are utilized and the results are recorded as cells per cubic mm. aqueous humor or vitreous.

The preparation is acceptable for veterinary or human use if the 48-hour postoperative evaluation of the monkey eye meets the following criteria:

| | |
|---|---|
| Cornea: | no haze, which indicated no swelling. |
| Iris: | no sign of inflammation. |
| Lens: | no damage caused by the injection needle. |
| Anterior Chamber: | flare: none or slight; total cell count: < 200/mm³. |
| Vitreous: | no blood or foreign body as observed in ophthalmoscope; haze: none or slight haze, but clear fundus; flare: none or slight, as evaluated by slit lamp; cells: none or few as evaluated by slit lamp, if counted: < 200/mm³ of undiluted vitreous. |
| Retina: | with indirect ophthalmoscope, no pathological changes observed; no bleeding or scars observed. |
| Choroid: | with indirect ophthalmoscope, no bleeding observed. |

(g) Sterile and Pyrogen Free

The sterility of the HUA preparation is demonstrated by standard methods using Tryptic Soybean Broth and Fluid Thioglycollate Media. The presence of endotoxin in the product was studied using the Limulus coagulation method. [Reinhold et al, Proc. Soc. Exp. Biol. Med. 137 (1) 334-340 (1971).] The product is negative for endotoxin.

(h) Non-antigenic

Published data [Richter, Int. Arch. Allergy 47:211-217 (1974)] show that purified HUA is not antigenic.

DESCRIPTION OF THE PREFERRED EMBODIMENTS

The process by which the hereinabove described product is prepared will now be discussed in detail.

The process of the invention comprises five major stages, each of which has one or more particular objectives. These stages are:

I Collection and Storage of Source Material,
II Extraction of HUA from Source Material,
III Deproteinization of the HUA Extract,
IV Removal of Impurities Which Cause Biological Reactions, and
V Sterilization of Purified HUA.

The several stages each comprise a series of steps which will now be described.

STAGE I

Healthy roosters (aged 6 months to 3 years, and only from breeds having large combs) are sacrificed by bleeding from the carotid artery. During this step the combs must be bled until most of the blood is removed and they become paler in color. The combs are cut off at the base, washed under running cold tap water, and scrubbed with a brush. The tips and ends of the combs are then trimmed off and discarded.

Alternately, human umbilical cords can be used. If so, within 10 minutes after birth human umbilical cords (only from healthy pregnancies) are washed in running tap water until all blood is removed from the surface and most of the blood in the vessels is pressed out.

After cleaning, the source tissue is frozen and stored in well-sealed Teflon ® containers at −40° to −20° C. to prevent evaporation and exposure to foreign materials where it may be kept for up to 12 months. The frozen tissue is then cut into thin pieces, after which it is immersed in 95% ethanol denatured with chloroform, which is a bacteriostatic agent (no more than 1 kg. of tissue per 4 liters of ethanol). The material is shaken for about 24 hours and the ethanol is decanted and discarded. The tissue is again immersed in 95% ethanol (without the bacteriostatic agent), in the same proportions and shaken for 48 hours after which the ethanol is decanted and discarded. If the ethanol is at all colored, the immersion and shaking steps are repeated with fresh 95% ethanol until it is clear. The tissue is now ready for further processing, although if desired, it can be stored at about 4°–22° C. in fresh 95% ethanol for up to 24 months.

The most significant aspect of the Stage I processing is the cutting of the tissue into small pieces, and the repeated extractions with fresh 95% ethanol. This allows efficient exposure of the tissue to the ethanol extraction solution. The reason for this is that the source tissue contains blood products which, in combination with oxygen, can cause degradation of the HUA in the subsequent water extraction steps. The efficiency of this initial cleaning step allows production of molecular weights significantly higher than the minimum 750,000 noted above.

STAGE II

The cut-up tissue is removed from the ethanol solution and immersed in an extraction solution consisting of 20 parts distilled water and 1 part chloroform (by volume). For each 2.5 kg. of cut combs, 10.5 liters of solution (10 liters distilled water and 0.5 liter chloroform) are used. The cut tissue is kept in this solution for about 24 hours to enable it to swell, after which an additional 15.75 liter portion of the above solution is added thereto.

Alternately, the swollen tissue may be homogenized in a meat grinder constructed of stainless steel to further reduce the size of the tissue pieces being extracted, after which the additional extraction solution is added thereto. The solution is then alternately stirred and permitted to settle over a 24 hour period at 4°–25° C. using a stirrer constructed of an inert material, such as Teflon R, after which the tissue is separated from the solution by filtration through a nylon cloth. The filtrate is collected in an all glass container. The separated tissue is then extracted with two more individual portions of 15.75 liters of water-chloroform, with 24 hour stirring and settling periods for each such extraction. The material is filtered through a nylon cloth and the filtrate is collected in an all glass container after each such extraction. The three water-chloroform extracts are combined and are now ready for further processing.

The major objective of Stage II is to obtain the highest possible yield of HUA from the tissue without degrading the macro-molecule to a lower molecular weight. Hyaluronic acid is extra-ordinarily sensitive to degradation due to shear and oxidation catalyzed by impurities and metal ions. I have found that the use of a series of extractions of the cut up tissues maintains high yields and decreases the chance of degradation in large scale production.

STAGE III

To the combined water-chloroform extracts obtained at the conclusion of Stage II, there is then added sufficient saturated NaCl solution or solid crystalline NaCl to achieve a 10% NaCl solution. An equal volume of chloroform is added and then the entire mixture is stirred at 4°–25° C. sufficiently to ensure complete and intimate contact between the chloroform phase and the aqueous phase but without excess shear which will cause significant degradation of the HUA macromolecules. I have found that stirring 15 liters of the mixture (7.5 liters aqueous solution and 7.5 liters of chloroform) in a 12-inch diameter unbaffled jar with a 7-inch pitched blade Teflon ® coated propeller for 3–5 hours at about 120–300 rev./min. provides sufficient mixing of the two phases without degradation of the HUA macromolecules. Substitution of different configurations of mixers and volumes of mixture to be stirred would be expected to alter the mixing conditions. Thereafter, the mixture is allowed to separate into aqueous and organic (chloroform) phases. The chloroform phase and the interphase are discarded. The pH of the aqueous phase is adjusted to 4.0–5.0 by adding dilute HCl. To the thusly acidified aqueous phase, an equal volume of chloroform is added and the mixture is again stirred sufficiently to ensure intimate contact between the HUA and protein in the aqueous phase and the chloroform phase. I have found again that 3–5 hours stirring under the conditions noted above is sufficient. The phases are again allowed to separate and the chloroform phase and the interphase are discarded. The procedure is again repeated with an additional volume of chloroform, followed by stirring and separation of the phases as before. The chloroform phase is again discarded. If necessary, the chloroform extraction is repeated following the above procedure until the chloroform layer is clear. The remaining acidified aqueous phase is retained for further processing in Stage IV.

The major objective of Stage III is to highly purify the HUA in the aqueous phase and remove other tissue impurities, such as, proteins and nucleotides under acid pH conditions without significant degradation of the HUA macromolecules. The number of repeated extractions with chloroform will vary with the efficiency of mixing and thus with the type of mixer employed and the volume of mixture to be stirred. As an alternate to repeated acid chloroform extractions, the aqueous solution may be treated with enzymes to assist in removal of tissue impurities. For example, after the second acid chloroform extraction I have added 50–100 mg. each of DNase and RNase to the aqueous phase. The solution is stirred under the above noted condition for 24 hours. Then the pH of the solution is raised to 6.0–7.0 and 50–100 mg. Pronase ® is added to the solution. The solution is stirred for 48 hours. The aqueous phase is then ready for further processing in Stage IV.

STAGE IV

The acidified (pH 4.5) aqueous phase obtained in Stage III is diluted with 0.1 N NaOH in an amount sufficient to raise the pH to 6.0–7.0, after which a volume of chloroform equal to that of the diluted aqueous phase is added thereto. Alternately, if Pronase ® treatment has been included in Stage III, additional NaOH will not be necessary as the solution is already at pH 6–7. The resulting mixture (two-phase system) is then stirred at about 20°–40°. sufficiently to ensure complete and intimate contact between all HUA macromolecules in the aqueous phase and the chloroform phase. I have found that under the above noted mixing conditions at least about 5 days are required in order to fully separate the inflammatory and non-inflammatory HUA macromolecules. At the conclusion of this extended stirring period, the two phases are allowed to separate and the chloroform phase is discarded. The aqueous phase, containing purified HUA from which the inflammation causing agent or agents have been removed is now ready for further processing in Stage V. The most critical step in Stage IV, and indeed, in the entire process, is the efficient but not excessive mixing of the chloroform and purified HUA phases, inasmuch as it is that step that effects complete removal of the unknown inflammatory agent(s).

Alternately, in addition to the above described extended chloroform extraction, separation of the inflammatory and non-inflammatory HUA macromolecules may be assisted by high speed centrifugation of the aqueous phase at about 70,000 to 110,000 g. force for about 4 hours.

STAGE V

The solution obtained at the conclusion of Stage IV is filtered through an inert Teflon ® sterilizing filter (pore size 0.2 μm); Millipore Corp. To the filtrate there are then added 3 volumes of ethanol to precipitate out the HUA which is thereafter dissolved in 1.5 liters of double distilled water containing 0.1 M NaCl. To this solution there are then added 3 volumes of ethanol to again precipitate out the HUA. The precipitated HUA is again dissolved in 1.5 liters of double distilled water and 1.0 M NaCl containing 1% of a chemical sterilizing agent such as cetyl pyridinium chloride. To this solution, 3 volumes of ethanol are added to again precipitate out the HUA. The dissolution in double distilled water and 0.1 M NaCl and the precipitation with ethanol are repeated twice more, after which the precipitated HUA is again dissolved in double distilled water and 0.1 M NaCl and then again precipitated, but this time with 3 volumes of acetone. The thusly precipitated HUA is washed three times with separate 0.5 liter portions of sterilized acetone, after which the precipitated HUA is dried under vacuum. The dried HUA is finally dissolved in a sterile physiological buffer solution containing 8.1661 g. NaCl, 0.4003 g. $Na_2HPO_4.7H_2O$ and 0.04455 g. $NaH_2PO_4.H_2O$ per liter of pyrogen-free double distilled water. The product may now be packaged in any convenient form such as pre-packaged syringes containing a jelly-like viscous solution of HUA.

By following the above described procedure, the HUA product of the invention (identified as Lot C2114) was produced. Five kilograms of trimmed rooster comb were treated yielding 3.97 g. of HUA product. Analysis of this HUA revealed the following properties:

(a) molecular weight: 1,586,000 limiting viscosity number: 2470
(b) protein content: 0.4%
(c) $A_{257}$: 0.243 $A_{280}$: 0.198
(d) kinematic viscosity: 37,091
(e) molar optical rotation: $-11 \times 10^3$ degree $cm^2$/mole (of disaccharide)
(f) cells/$mm^3$ aqueous humor: in two separate tests the results were 0 and 11 cells respectively
(g) sterile Biological Activity of the Purified HUA and Uses Thereof Laboratory studies[1] have shown that HUA inhibits cell migration and multiplication of certain cells in vitro. This biological activity increases with increasing HUA molecular weight, increasing conformational order of the HUA molecule, increasing HUA concentration, and increasing kinematic viscosity of HUA solutions. Consequently, in order to achieve significant biological activity, HUA solutions must be of high viscosity, high HUA concentration, and must contain high molecular weight and highly conformationally ordered HUA molecules. In summary, these in vitro studies have shown that HUA is a cell immobilizing agent of lymphomyeloid cells; and that HUA inhibits the stimulation of lymphocytes.

(1) Balazs et al, in Biology of the Fibroplast, pp. 237–252, Academic Press, London, 1973; Darzynkiewicz et al, Exptl. Cell Res., 66 (1971) pps. 113–123.

Therapeutic Uses of Purified HUA

The sterile HUA product of the invention has therapeutic application in three major areas.

1. Prevention of fibrous tissue formation

HUA influences the invasion and activity of cells participating in the acute and chronic inflammatory processes. Thus, the HUA of the invention can be implanted when prevention of excess fibrous tissue formation and consequent development of adhesion and scars are not desirable.

a. In joints and bursae the HUA of the invention can be used to replace the synovial fluid in a synovial space to impede the development of intraarticular fibrous tissue (pannus, ankylosis, adhesions) and to support the healing process of cartilage and synovial tissue. As used herein, the term "synovial space" is intended to mean that space which separates joints, tendons and/or bursae. Thus, the primary indication for HUA implantation in the joints and adjacent spaces is traumatic arthritis, osteoarthritis and bursitis[1].

(1) Helfet, A. J. in Disorders of the Knee, J. D. Lippincott Co. (1974) pps. 175–194; Peyron et al, Pathologie Biologie 22, pps. 731–736 (1974).

In the chronic inflammatory processes of these tissues (rheumatoid arthritis), the HUA of the invention can be used as a vehicle for any kind of intraarticular medication to protect the articular cartilage from the possible harmful effects of the particular drug used, and to prolong the effect of the drug by decreasing its diffusion out of the articular space.

b. In arthroplasty, osteotomy and all types of intraarticular surgery, the HUA of the invention can be used to protect the articular cartilage surfaces from postoperative injury and from the possible harmful effect of prosthetic surfaces, to prevent excess fibrous tissue formation and to promote the normal healing of the soft tissues and cartilage.

c. The present HUA can also be implanted between tendons and their sheaths to minimize adhesion formation after any surgical procedure[2].

(2) Rydell et al, Clinical Orthopaedics, No. 80, October, 1971, pps. 25–32.

d. HUA can also be implanted around peripheral nerves and nerve roots after injury or surgery when damage to the connective tissue around the nerve is extensive and excessive scar formation is expected. Implantation of HUA around the healing (regenerating) nerve can protect it from invasion by connective tissue cells.

e. Implantation of HUA between mesothelial, pericardial and pleural sheets and on fasciae is indicated when the prevention of adhesion formation between two endothelial or connective tissue membranes is desired.

f. Implantation of HUA into the vitreous is indicated after extensive intravitreal surgery (removal of hemorrhages, opacities, etc.) to prevent excessive cellular reaction, and development of fibrous bands and preretinal tissue membranes.

g. The aqueous humor may be replaced by HUA after various intraocular surgical procedures that might cause cellular invasion of the anterior chamber, which would endanger the regeneration and function of the iris, ciliary body and corneal endothelium.

2. Separation of tissue surfaces with a biological prosthesis

HUA can be used to separate tissue surfaces. The elastoviscous quality of HUA and its biological origin provide two advantages. First, it serves as a mechanical protector of the tissue during surgical manipulation and postoperatively; second, it does not cause inflammation, foreign body reaction, or development of a connective tissue capsule.

a. The use of HUA in retinal detachment surgery has two purposes. It provides the surgeon with a visco-elastic tool in the manipulation necessary for reattachment of the retina, and it facilitates the intraocular wound healing by preventing excessive fibrous tissue formation and development of intravitreal scar tissue (preretinal organizations, membranes, bands)[1].

[1] Regnault et al., Mod. Probl. Ophthal., Vol. 12, pps. 378–383 (1974); Acta Ophthalmologica, Vol. 49 (1971) pps. 975–6; Edmund, J., Mod. Probl. Ophthal., Vol. 12, pps. 370–377 (1974).

b. The use of HUA as a biological prosthesis in the anterior chamber is indicated after cataract surgery in order to push back prolapsed vitreous and, after resection of the anterior face of the vitreous, to provide separation between the vitreous and cornea.

c. This biological prosthesis (HUA) can be used in the anterior chamber after keratoplasty to prevent adhesion formation between the corneal wound and the iris.

d. This biological prosthesis (HUA) can be used for the separation of tissue surfaces (endothelial or connective tissue) to promote fistula formation. When a new channel for liquid passage must be formed or a blocked channel has to be re-formed, the insertion of HUA jellies or dry membranes can help prevent the development of scar tissue during healing. Development of fistualae between the anterior chamber and subconjunctival space may be facilitated in this way in glaucoma surgery.

3. Protection of skin wounds

HUA can act as a barrier to water and microorganisms when it is used to cover extensive skin wounds caused by chamicals or heat. HUA in wet form or as a dry membrane, which becomes hydrated after contact with the wound, can provide effective protection against excessive water loss and can sieve out bacteria that do not have hyaluronidase activity.

Undoubtedly, other uses and applications of the ultrapure, non-inflammatory HUA of the invention might occur to those skilled in the art and thus, the foregoing brief description of the therapeutic uses of the HUA of the invention does not cover all the possible medical uses, nor does it intend to imply that in all the medical problems mentioned, HUA is, or will provide, the final remedy.

Variations and modifications can, of course, be made without departing from the spirit and scope of the invention.

Having thus described my invention what I desire to secure by Letter Patent and hereby claim is:

1. A sterile, pyrogen-free, protein-free, non-antigenic, hyaluronic acid fraction having an average molecular weight of at least about 750,000, a protein content of less than 0.5% by weight, ultraviolet light absorbance of a 1% solution of the sodium salt thereof of less than 3.0 at 257 nanometers wavelength and less than 2.0 at 280 nanometers wavelength, a kinematic viscosity of a 1% solution of the sodium salt thereof in physiological buffer of greater than about 1000 centistokes and a molar optical rotation of a 0.1–0.2% solution of the sodium salt thereof in physiological buffer of less than $-11 = 10^3$ degree — $cm^2$/mole (of disaccharide) measured at 220 nonometers; and which is characterized by infiltration by no more than about 200 white blood cells per $mm^3$ of aqueous humor of the owl monkey eye when one milliliter of a 1% solution of the sodium salt of said fraction dissolved in physiological buffer is implanted in the vitreous replacing about one-half the existing liquid vitreous.

2. A fraction according to claim 1, wherein the molecular weight is at least about 1,200,000 and the kinematic viscosity is greater than about 10,000 centistokes.

3. The sodium salt of the hyaluronic acid fraction according to claim 1.

4. A method of improving pathological joint function in an animal by relieving pain, reducing inflammation and effecting the healing of an intraarticular wound associated therewith, said method comprising introducing by injection into an affected joint, an amount of hyaluronic acid according to claim 1, sufficient to increase the normal hyaluronic acid concentration in said joint by at least 5 times.

5. A method of enhancing normal joint and tendon function in an animal by lubricating said joint or tendon against excess stress during movement, said method comprising introducing into the synovial space associated with said joint or tendon an amount of the hyaluronic acid according to claim 1 sufficient to increase the normal hyaluronic concentration in said synovial space by at least 5 times.

6. A method according to claim 5, wherein the concentration is increased by a factor of 5 to 50 times.

7. A method according to claim 5, wherein said animal is a racing animal.

8. A method of preventing post-operative adhesion which may occur between healing tissues during the normal healing process, said method comprising introducing into a surgical site, either during surgery or post-operatively, an amount of the hyaluronic acid according to claim 1 sufficient to establish and maintain at the surgical site a hyaluronic acid concentration of at least about 1% for a period of about 24 hours post-operatively.

9. A method of separating healing tissues and maintaining said separation during the normal healing process after surgery, said method comprising introducing into a surgical site, either during surgery or post-operatively, an amount of the hyaluronic acid according to claim 1 sufficient to establish and maintain at the surgical site a hyaluronic acid concentration of at least about 1% for a period of about 24 hours post-operatively.

10. A method of protecting a layer of tissue during surgery on an adjacent layer of tissue, said method comprising introducing into the surgical site an amount of the hyaluronic acid according to claim 1 sufficient to prevent dislocation and movement of said tissue by providing a viscoelastic medium at the surgical site during said surgery.

11. A composition comprising the fraction according to claim 1 dissolved in a sterile physiological buffer solution containing NaCl, $Na_2HOP_4.7H_2O$ and $NaH_2PO_4.H_2O$ in pyrogen-free double distilled water.